US008076328B2

(12) United States Patent
Häuser-Hahn et al.

(10) Patent No.: US 8,076,328 B2
(45) Date of Patent: Dec. 13, 2011

(54) USE OF FUNGICIDES FOR THE TREATMENT OF FISH MYCOSES

(75) Inventors: Isolde Häuser-Hahn, Leverkusen (DE); Klaus Stenzel, Düsseldorf (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/595,034

(22) PCT Filed: Apr. 8, 2008

(86) PCT No.: PCT/EP2008/002758
§ 371 (c)(1),
(2), (4) Date: Oct. 7, 2009

(87) PCT Pub. No.: WO2008/128640
PCT Pub. Date: Oct. 30, 2008

(65) Prior Publication Data
US 2010/0063039 A1 Mar. 11, 2010

(30) Foreign Application Priority Data
Apr. 20, 2007 (EP) .................... 07106656

(51) Int. Cl.
*A01N 43/88* (2006.01)
*A01N 43/64* (2006.01)
*A01N 43/50* (2006.01)
*A01N 43/76* (2006.01)
*A01N 43/40* (2006.01)
*A01P 3/00* (2006.01)

(52) U.S. Cl. ............ 514/229.2; 544/384; 544/398; 544/376; 544/345

(58) Field of Classification Search .......... 544/384; 514/229.2, 398, 376, 345
See application file for complete search history.

(56) References Cited

U.S. PATENT DOCUMENTS

| 3,755,349 | A | | 8/1973 | Timmler et al. |
|---|---|---|---|---|
| 6,075,023 | A | * | 6/2000 | Dohmen et al. ............ 514/241 |
| 6,160,023 | A | | 12/2000 | Braidwood |
| 2007/0105915 | A1 | * | 5/2007 | Gouot et al. .............. 514/357 |

FOREIGN PATENT DOCUMENTS

| AU | 2003-250752 A8 | 1/2004 |
|---|---|---|
| DE | 2 037 610 | 2/1972 |
| DE | 102 37 740 A1 | 3/2004 |
| EP | 0 322 351 A2 | 6/1989 |
| JP | 47-19191 | 12/1967 |
| JP | 57-116012 A | 7/1982 |
| JP | 61-267521 A | 11/1986 |
| JP | 36-98745 B2 | 2/1996 |
| WO | WO 95/18534 A1 | 7/1995 |
| WO | WO 97/06690 A1 | 2/1997 |
| WO | WO 98/05311 A1 | 2/1998 |
| WO | WO 2004/002574 A1 | 1/2004 |
| WO | WO 2006-128863 A1 | 12/2006 |

OTHER PUBLICATIONS

Breuer (Ecotoxicological profile of the fungicide Fluoxastrobin, Pflanzenschutz-Nachrichten Bayer 2004, vol. 57 pp. 319-336).*
Lee (Coparative metabolism of famoxadone in fish, plants and animals, Pestic Sci, 1999, vol. 55: pp. 589-594).*
Alderman, D.J., "Malachite green: a review," *Journal of Fish Diseases* 8:289-298 (1985).
Briggs, G., et al., "The discovery and chemistry of fluopicolide: a new standard for oomycetes disease control," *Pflanzenschutz-Nachrichten Bayer* 59:141-152 (2006).
Buchenauer, H., "Comparative studies on the antifungal activity of triadimefon, triadimenol, fenarimol, nuarimol, imazalil and fluotrimazole in vitro," *Journal of Plant Diseases and Protection* 86:341-354 (1979).
Berg, L.R., et al., "Effects of Triarimol and Tridemorph on Sterol Biosynthesis in *Saprolegnia ferax*," *Lipids* 18:448-452 (1983).
Campbell, R.E., et al., "In vitro screening of novel treatments for *Aphanomyces invadans*," *Aquaculture Research* 32:223-233 (2001).
Jarowaja, N., "Selection of fungicides for sugar beet seed treatment," *Chemical Abstracts*, Accession No. 1399 (1981).
Lamberth, C., "Fungizide gegen Kartoffelfäule und Falschen Mehltau die nächste Generation," *Nachrichten Aus Der Chemie* 55:130-134 (2007).
Meyer, F.P., "Teratological and Other Effects of Malachite Green on Development of Rainbow Trout and Rabbits," *Transactions of the American Fisheries Society* 112:818-824 (1983).
Mitani, S., et al., "Antifungal Activity of the Novel Fungicide Cyazofamid against *Phytophthora infestans* and Other Plant Pathogenic Fungi in Vitro," *Pesticide Biochemistry and Physiology* 70:92-99 (2001).
Sanchez, J., et al. "Morphometric Assessment of Epidermal and Mucous-biofilm Changes Caused by Exposure of Trout to Chloramine-T or Formalin Treatment," *J. Comp. Path.* 118:81-87 (1998).

(Continued)

*Primary Examiner* — San-Ming Hui
*Assistant Examiner* — Kathrien Cruz
(74) *Attorney, Agent, or Firm* — Sterne, Kessler, Goldstein & Fox PLLC

(57) ABSTRACT

Process for the protection of fish and invertebrates and all their stages of development against or for the treatment of mycoses caused by fungi of the genera *Saprolegnia, Aphanomyces, Achlyaflagellata* and other species important in aquacultures by use of 2-[[[[1-[3-(1-fluoro-2-phenylethyl)oxy]phenyl]ethylidene]amino]oxy]methyl]alpha-(methoxyimino)-N-methyl-alphaE-benzeneacetamide, amisulbrom, cyazofamid, enestrobin, famoxadone, fenamidone, fluoxastrobin, orysastrobin, picoxystrobin and pyribencarb. This use leads to an inhibition or destruction of pathogenic fungi.
The composition, comprising at least one fungicide selected from the abovementioned group for use in fish farming and keeping is suitable for the prophylaxis and therapy of diseases of fish in aquaculture, in breeding ponds, breeding tanks, aquariums, natural stretches of game fish waters, ponds, and marine fish farms. Addition to the water and feed and direct application are the associated use forms. The addition of the composition according to the invention to the water decreases fungal infections of spawn and fish.

1 Claim, No Drawings

OTHER PUBLICATIONS

Srivastava, M.K., "Synthesis of some $N^1$-phenyl-$N^3$-[2-aryl/aryloxymethyl-1,3,4-oxa(thia)diazol-2-yl]sulphonyl ureas as potential pesticides," *Bulletino Chimico Farmaceutico* 139:161-166 (2000).

Srivastava, S., et al., "Toxicological effects of malachite green," *Aquatic Toxicology* 66:319-329 (2004).

Tynan, J., et al., "Miconazole: An effective antifungal agent for plant tissue Culture," *Plant Cell Tissue and Organ Culture* 32:293-301 (1993).

Young, D.H., et al., "Antifungal Properties of Taxol and Various Analogues," *Experitentia* 48:882-885 (1992).

Young, D.H., et al., "Laboratory studies to assess the risk of development of resistance to zoxamide," *Pest Management Science* 57:1081-1087 (2001).

Young, D.H., et al., "Mode of Action of Zoxamide (RH-7281), a New Oomycete Fungicide," *Pesticide Biochemistry and Physiology* 69:100-111 (2001).

Yuasa, K., and Hatai, K., "Investigation of Effective Chemicals for Treatment of Saprolegniasis Caused by *Saprolegnia parasitica*," *Journal of Antibact. Antifung. Agents* 24:27-31 (1996).

Database WPI Abstract, Control Agent for Carp Diseases Contain Kasugamycin Salt as Active Component, *Accession* No. 1987-010537 (1986).

International Search Report for International Application No. PCT/EP2008/002758, mailed Jul. 4, 2008.

International Search Report for International Application No. PCT/EP2008/002830, mailed Oct. 20, 2008.

English language abstract of JP 57-116012 A, Patent Abstract of Japan, Japanese Patent Office (1982) (Document FP5).

English language equivalent of DE 102 37 740 A1 (2004) (Document FP12).

\* cited by examiner

USE OF FUNGICIDES FOR THE TREATMENT OF FISH MYCOSES

The invention relates to a process for the prophylaxis and treatment of mycoses in fish and invertebrates and all stages of development thereof, caused by fungi of the genera *Saprolegnia, Achlya, Aphanomyces* and other species important in aquacultures (called pathogenic fungi below) by the use of at least one fungicide selected from the following group 2-[[[[1-[3-(1-fluoro-2-phenylethy)oxy]phenyl]ethylidene]amino]oxy]methyl]alpha-(methoxyimino)-N-methyl-alphaE-benzeneacetamide, amisulbrom, cyazofamid, enestrobin, famoxadone, fenamidone, fluoxastrobin, orysastrobin, picoxystrobin and pyribencarb.

The invention likewise relates to a composition comprising at least one fungicide selected from the following group 2-[[[[1-[3-(1-fluoro-2-phenylethyl)oxy]phenyl]ethylidene]amino]oxy]methyl]-alpha-(methoxyimino)-N-methyl-alphaE-benzeneacetamide, amisulbrom, cyazofamid, enestrobin, famoxadone, fenamidone, fluoxastrobin, orysastrobin, picoxystrobin and pyribencarb for the prophylaxis and therapy of mycoses in fish and invertebrates and all their stages of development, caused by fungi of the genera *Saprolegnia, Achlya, Aphanomyces* and other species important in aquacultures (called pathogenic fungi below). The composition is used in fish farming and in fish keeping, in all stages of development, especially for prophylactic and therapeutic use in diseased and stressed fish.

The invention further relates to the use of a composition for the antimycotic treatment of fish spawn.

On account of the globally increasing need for fish, these are increasingly kept in aquaculture. By way of example, but not restrictively, the following fish species may be mentioned as relevant for aquaculture: catfish, trout, salmon, Pangasius and perch. On account of the proximity of the fish to one another, aquacultures of this type are extremely susceptible to pathogens, in particular pathogenic fungi. Pathogenic fungi which attack both fish and fish eggs and other stages of development belong to the following genera: *Saprolegnia hypogyna, S. ferax, S. australis, S. declina, S. longicaulis, S. mixta, S. parasitica, S. sporangium, S. variabilis, Aphanomyces invadans* and *Achlyaflagellata* spp.

As a result of mycoses, high economic losses result in the farming and keeping of productive and ornamental fish and also of crustaceans and other invertebrates (Bruno, D. W., Wood, B. P., 1999: *Saprolegnia* and other Oomycetes. In: Woo, P. T. K, Bruno, D. W. (Ed): *Fish Diseases and Disorder. Vol. 3 Viral, Bacterial and fungal infections.* CAB International, Wallingford).

As yet, however, only a few substances are known which are suitable for the control of fish mycoses.

In the past, malachite green was often used as an active substance for the prophylaxis and therapy of mycoses. On account of its carcinogenic, mutagenic and teratogenic properties, this substance is only tolerated in Germany, however, for the treatment of fish eggs, but is not permitted for the treatment of fish (Meyer, F. P.; Jorgenson. T. A., 1983: *Teratological and other effects of malachite green on development of rainbow trout and rabbits. Trans. Am. Fish. Soc.* 112, 818-824, (*Bundesinstitut fur gesundheitlichen Verbraucherschutz and Veterinärmedizin [Federal Institute for Consumer Protection of Health and Veterinary Medicine]*, 2002). As malachite green is a dye, it can lead to discolouration of the water and of the treated fish. In addition, malachite green has a long half-life, so that it can result in residues in the fish which are to be consumed later (D. J. Alderman in *Journal of Fish Diseases* 8. (1985) 289-298).

Today, formalin is furthermore employed which, although it has a certain fungicidal action against pathogenic fungi, is not satisfactory in practical use and moreover causes occupational safety problems, in particular in closed systems.

In DE 10237740, the use of natural and synthetic humic substances in fish farming is described.

It is already known from DE 2 037 610 that certain benzylimidazoles act in vitro against *Saprolegnia parasitica*. However, nothing about potential application in fish farming is mentioned.

In CN 1472448, fungicidally active herb formulations are described for use as agents against saprolegniasis in fish, shrimps and crabs. The formulations contain Galla Chinensis 40-70, Cortex Phellodendri (Phellodendron chinense and/or Phellodendron amurense) 10-30, Paeonia suffruticosa bark 10-30, and Houttuynia cordata 10-30 wt %.

Tea extracts comprising various polyphenols can also be employed (JP 3698745).

In WO 04 002574, enzyme mixtures comprising glucanases are described for the prophylaxis and therapy of mycoses in fish and development stages thereof (eggs).

In WO 98 05311, bromopol (bromo-2-nitropropane-1,3-diol) is used for the control of various diseases of aquatic organisms, in particular salmon and their eggs.

In addition, the use of chlorine dioxide (WO 95 18534), 3-phenoxycarbonylmethoxy-1,1,2-triiodo-1-propene (JP 57116012) and 2-pyridinethiol 1-oxide (JP 47019191) against *Saprolegnia* diseases is known.

The use of kresoxim-methyl for the control of fish mycoses is known from WO 97006690.

However, on the one hand the efficacy of these substances, especially at low doses, is often not adequate. On the other hand, on account of piscotoxic properties the restriction of the compatibility of the treatment can occur, so that an efficacious dose cannot adequately be employed. Moreover, an exact dose, in particular of herb or tea extracts or enzyme mixtures is difficult on account of their varying active substance contents. In addition, the use of these preparations is suitable only for individual fish species and diseases. Moreover, the use of the preparations is often restricted to a period long before fishing ('harvesting') on account of their toxic properties, as long waiting times are necessary between use and the consumption of the fish.

Since the ecological and economic demands on modern antimycotics are continuously increasing, for example as far as spectrum of action, toxicity, selectivity, application rate, residue formation and convenient producibility are concerned, there is the continual task of developing novel antimycotics, which have advantages compared to the known antimycotics, at least in subareas.

Moreover, these substances have toxic side effects. The use of, for example, formalin, chloramine T and malachite green oxalate is often associated with a number of side effects and risks, for instance it has carcinogenic, mutagenic, chromosome-damaging and teratogenic potential, acts as a respiratory poison, and in addition histopathological sequelae and multiorgan damage and significant alterations of biochemical blood parameters occur (Sanchez et al. 1998; Srivastava et al. 2004; from St. Heidrich dissertation, 2005).

In addition to the pure disinfectants, other substances are also in use. These include acetic acid (for immersion treatments), sodium chloride and calcium chloride (as osmoregulatory treatments), sodium carbonate and carbon dioxide (for the anaesthetization of fish) and sodium sulphite (for the improvement of egg-laying) and povidone iodine (for the disinfection of the surface of the fish spawn).

The reasons for the disadvantages of conventional prophylactics and therapeutics results from their long-term extensive and in some cases imprudent use, e.g. of antibiotics, chemotherapeutics and triphenyl dyes, inter alia, active substances for the elimination of bacterial, parasitic and environmentally related diseases and for increasing the yield. From this use, in some cases unfavourable resistance situations developed for the treatment of diseases in animals and humans. In addition, the use of conventional compositions is often associated with severe side effects, risks and environmental damage.

Accordingly, in the field of aquaculture there is an increased need for efficient means of controlling pathogens which reduce the productivity of commercial fish production. In the case of the occurrence of fish diseases, early intervention with mainly prophylactic character and avoidance and alleviation of disease-inducing factors plays an ever greater role. For this reason, the search for alternative treatment possibilities has outstanding importance. The means employable should control a broad pathogen spectrum and meet existing safety guidelines. The present invention fulfils these criteria and produces further advantages.

It has now surprisingly been found that at least one fungicide selected from the following group 2-[[[[1-[3-(1-fluoro-2-phenylethyl)oxy]phenyl]ethylidene]amino]oxy]methyl] alpha-(methoxyimino)-N-methyl-alphaE-benzeneacetamide, amisulbrom, cyazofamid, enestrobin, famoxadone, fenamidone, fluoxastrobin, orysastrobin, picoxystrobin and pyribencarb is very highly suitable for the purpose of both preventing and treating mycoses in fish, shrimps, crabs and other invertebrates and all their stages of development, caused by fungi of the genera *Saprolegnia, Achlya, Aphanomyces*, in particular fungal diseases caused by *Saprolegnia* spp. The compositions according to the invention are suitable for the control of mycoses which are caused by *Saprolegnia* and/or *Achlya* and/or *Aphanomyces* species.

Compared to the substances or treatment methods known from the prior art, the use of the fungicides mentioned in the treatment has the following advantages: they show good efficacy and do not accumulate to an undesired extent in the fish body, they have favourable ecological and other toxicological properties and do not show any unacceptable effects on the biocoenoses.

The invention thus relates to the use of at least one fungicide selected from the following group 2-[[[[1-[3-(1-fluoro-2-phenylethyl)oxy]phenyl]ethylidene]amino]oxy]methyl] alpha-(methoxyimino)-N-methyl-alphaE-benzeneacetamide, amisulbrom, cyazofamid, enestrobin, famoxadone, fenamidone, fluoxastrobin, orysastrobin, picoxystrobin and pyribencarb for the control of fish mycoses in all fish populations and their stages of development, in particular those which are caused by *Saprolegnia* pathogens.

The fungicides used in the process according to the invention are already known as agrochemical active substances (cf., for example, Pesticide Manual, 13th edition).

Fish diseases play a role in fish farming and aquaculture, in aquaristics and in feral fish populations. Various types of disease can be distinguished here, such as hereditary diseases, infectious and parasitic diseases, injuries, water-related damage and damage due to stress factors in the keeping conditions. A complex interrelationship prevails between the defence abilities, the pathogens and the living conditions, which finally decides about the outbreak of infectious diseases. A large number of widespread fish diseases are caused by the attack of parasites. Parasites are also held responsible for approximately 50 percent of cases of death in young animals in aquaristics. Depending on the type of pathogen, attack by parasites can take place insidiously or explosively and make sure that many to all animals of a pool are affected by diseases. Fungi, bacteria and viruses can also cause diseases in fish.

The diseases caused by fungi are called mycoses. It can be a question of secondary infections here, i.e. that before the mycoses other diseases had already attacked the fish or the pool. Fungi can also live primarily parasitically. As fungi also have a walled boundary, mycoses which have penetrated into the skin can only be treated with difficulty.

*Saprolegnia* belongs to the class of the Oomycetes. Diseased fish show the following symptoms: they exhibit white, cotton wool-like, grey-white fungal infections on the surface. These fungi can often then colonize the fish if the protective mucous layer or the epidermis is injured. Such fungal proliferations can be the result of stab or bite wounds by other organisms or of mechanical injuries, but also due to the effects of temperature or waste water. Also endangered, however, are the fish eggs. The fungus occurs naturally in all stretches of fresh water and attacks debilitated fish. It often appears that particularly elderly male trout are strongly affected. *Saprolegnia* is both a weak parasite, which occurs secondarily, and a primary parasite, which can attack the fish and their eggs directly. It can incidentally attack all types of fish.

It is the aim of the invention to demonstrate areas of application in the avoidance and treatment of damage to fish which result in the case of fishing, transport and keeping, to improve the results in the breeding of fish and in egg treatments and to guarantee a trouble-free operation of facilities in aquaculture and aquaristics.

The fungicides can be present both in pure form and as mixtures of various possible isomeric forms, in particular of stereoisomers, such as E and Z, threo and erythro, and also optical isomers, such as R and S isomers or atropisomers, but if appropriate also of tautomers. The invention comprises both the pure isomers and their mixtures.

Defending on the type of substituents defined above, the abovementioned fungicides have acidic or basic properties and can form salts, optionally also internal salts. If the fungicides carry hydroxyl, carboxyl or other groups inducing acidic properties, these compounds can be reacted with bases to give salts. Suitable bases are, for example, hydroxides, carbonates, hydrogencarbonates of the alkali metals and alkaline earth metals, in particular those of sodium, potassium, magnesium and calcium, furthermore ammonia, primary, secondary and tertiary amines having ($C_1$-$C_4$-)-alkyl radicals, mono-, di- and trialkanolamines of ($C_1$-$C_4$)-alkanols, choline and chlorocholine. If the fungicides carry amino, alkylamino or other groups inducing basic properties, these compounds can be reacted with acids to give salts. Suitable acids are, for example, mineral acids, such as hydrochloric, sulphuric and phosphoric acid, organic acids, such as acetic acid or oxalic acid, and acidic salts, such as $NaHSO_4$ and $KHSO_4$. The salts obtainable in this way likewise have fungicidal properties.

The fungicides to be used according to the invention are mentioned above.

Preference is given to fungicides selected from the following group amisulbrom, cyazofamid, enestrobin, famoxadone, fenamidone, fluoxastrobin, orysastrobin, picoxystrobin and pyribencarb.

Particular preference is given to fungicides selected from the following group enestrobin, famoxadone, fenamidone, fluoxastrobin, orysastrobin and picoxystrobin.

Very particular preference is given to fungicides selected from the following group fenamidone and famoxadone.

Very particular preference is further given to fungicides selected from the following group enestrobin, orysastrobin and fluoxastrobin.

Preference is given in particular to fungicides selected from fenamidone and fluoxastrobin.

In the processes, uses and compositions according to the invention, both individual fungicides and two or more fungicides in combination can be selected.

According to the invention, the fungicides are added to the water of aquaculture facilities, e.g. to hatching facilities, breeding ponds, breeding tanks, round swimming pools, fattening pools, aquariums, stretches of natural game fish waters and marine fish farms and by their action the inhibition of growth or destruction of pathogenic fungi is caused. Aquaculture facilities in this sense are installations which are used for the raising of fish or vertebrates in fresh, brackish or salt water. The fungicides are added to the water. The dose is based upon the condition (organic pollution) of the water in the aquaculture facility, the activity of the fungicide and the stage of development of the fish to be treated. The activity level is maintained by continuous or batchwise addition, which suppresses existing mycoses and prevents the occurrence of new infections.

The application rates, depending on the type and stage of development of the fish and on the type of fungicide, are 0.1 μg/l to 1 g/l, preferably 1 μg/l to 100 mg/l, especially preferably 5 μg/l to 1 mg/l of active substance. Higher concentrations are in general not necessary, but can be useful in the treatment of egg, larval and juvenile stages, depending on the type of compound or application, particularly in artificial systems, such as, for example, breeding tanks or aquariums.

An action against mycoses is furthermore achieved in that the fungicides are employed not only in free form in the aqueous medium of the aquaculture facilities, but also bound to the surface (mucous membrane) of organisms to be protected or their eggs. This procedure is to be preferred if a high danger of infection makes a higher fungicide content necessary or in the case of a high water throughput of the aquaculture facility a continual addition of fungicide mixture is not possible. The binding is achieved by treatment of the animals or their eggs by a temporary preincubation at elevated fungicide concentrations, in addition to the fungicide mixture substances preferably being employed which increase binding of the fungicides.

The efficacious amount of a fungicide comprises exemplary dose rates for a fish of approximately 1 μg to 10 mg/kg/day, which can be administered in an individual dose or in the form of individual divided doses, such as 1 to 4 times per day. Preferably, the compounds are administered in a dose of less than 10 mg/kg/day, administered in an individual dose or in 2 to 4 divided doses.

The active substances can be administered directly or mixed before use with customary inert carriers. Fundamentally, those substances are suitable as inert carriers which facilitate or guarantee a homogeneous distribution of the active substance in the water or on the surface (mucous membrane) of organisms to be protected or their eggs.

Depending on their respective physical and/or chemical properties, the active substances can be converted into the customary formulations, such as solutions, emulsions, suspensions, powders, foams, pastes, granules, aerosols, very fine encapsulations in polymeric substances and in coating compositions for seeds, and ULV cold and warm mist formulations.

These formulations are produced in a known manner, e.g. by mixing the active substances with extenders, that is liquid solvents, liquefied gases under pressure and/or solid carriers, if appropriate using surface-active agents, that is emulsifying agents and/or dispersing agents and/or foam-generating agents. In the case of the use of water as an extender, it is also possible to use, for example, organic solvents as auxiliary solvents. Suitable liquid solvents are in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, e.g. petroleum fractions, alcohols, such as butanol or glycol, and their ethers and esters, ketones, such as acetone, methyl ethyl ketone, methyl isobutyl ketone or cyclohexanone, strongly polar solvents, such as dimethylformamide and dimethyl sulph-oxide, and water. By liquefied gaseous extenders or carriers, those liquids are meant which are gaseous at normal temperature and under normal pressure, e.g. aerosol propellants, such as halogenohydrocarbons and butane, propane, nitrogen and carbon dioxide. Suitable solid carriers are: e.g. natural ground minerals, such as kaolins, clays, talc, chalk, quartz, attapulgite, montmoril-lonite or diatomaceous earths and ground synthetic minerals, such as highly disperse silica, alumina and silicates. Suitable solid carriers for granules are: e.g. crushed and fractionated natural rocks such as calcite, pumice, marble, sepiolite, dolomite and synthetic granules of inorganic and organic meals, and granules of organic material such as sawdust, coconut shells, maize cobs and tobacco stalks. Suitable emulsifiers and/or foam-generating agents are: e.g. non-ionic and anionic emulsifiers, such as polyoxyethylene fatty acid esters, polyoxyethylene fatty alcohol ethers, e.g. alkylaryl polyglycol ethers, alkylsulphonates, alkylsulphates, arylsulphonates and protein hydroly-sates. Suitable dispersing agents are: e.g. lignin-sulphite waste liquors and methylcellulose.

It is possible to use in the formulations adhesives, such as carboxymethylcellulose, natural and synthetic pulverulent, granular or latex-like polymers, such as gum arabic, polyvinyl alcohol, polyvinyl acetate, and natural phospholipids, such as cephalins and lecithins, and synthetic phospholipids. Further additives can be mineral and vegetable oils.

It is possible to use colorants, such as inorganic pigments, e.g. iron oxide, titanium oxide and Prussian Blue, and organic dyestuffs such as alizarin dyestuffs, azo dyestuffs and metal phthalo-cyanine dyestuffs, and trace nutrients, such as salts of iron, manganese, boron, copper, cobalt, molybdenum and zinc.

The formulations in general contain between 0.1 and 95 percent by weight of active substance, preferably between 0.5 and 90%.

The invention relates to a process for the treatment of fish suffering from mycoses and all their stages of development with efficacious fungicides.

It is evident that the specific dose and the frequency of dosage can be varied for certain types of fish and depending on the stage of development, and depend on a large number of factors, including the efficacy of the specific compound used, the metabolic stability and the length of action of this compound, the species, the age, the weight, the general state of health, the sex and the food of the fish, the nature and the time of administration, the excretion rate and the severity of the particular condition.

The present invention thus makes available a veterinary medicament which comprises at least one fungicide with which *Saprolegnia* diseases or other fish diseases can be treated, in an amount efficacious for this purpose, and a pharmaceutically tolerable carrier or a pharmaceutically tolerable diluent. The compositions according to the invention can contain other therapeutic agents, as described below, and can be formulated, for example, using conventional solid or liquid carriers or diluents, such as pharmaceutical additives of a type which is suitable for the desired administration (for example excipients, binding agents, preservatives, stabilizers, flavourings etc.) according to techniques which are well known in the area of pharmaceutical galenics or demanded by accepted pharmaceutical practice.

The efficacious fungicides described above can be administered by any desired suitable means, for example orally, such as in the form of tablets, capsules, granules or powders, sublingually, buccally, parenterally, such as by means of subcutaneous, intravenous, intramuscular or intrasternal injection or infusion techniques (e.g. as sterile, injectable, aqueous or non-aqueous solutions or suspensions), topically, such as in the form of a cream or ointment or in dose unit formulations which contain non-toxic, pharmaceutically tolerable carriers or diluents. The fungicides can be administered, for example, in a form which is suitable for immediate release or prolonged release. The immediate release or the prolonged release can be achieved by the use of suitable medicaments which contain the efficacious fungicides described above or, especially in the case of prolonged release, by the use of devices such as subcutaneous implants or osmotic pumps. The compounds can also be administered liposomally. For example, the active substance can be used in a composition such as a tablet, a capsule, a solution or suspension which contains approximately 5 to approximately 500 mg per unit dose of a compound or mixture of compounds from the list of the abovementioned fungicides, or in a topical form (0.01 to 5% of fungicide, one to five treatments per day). It can be mixed in a conventional manner with a physiologically tolerable carrier, excipients, binding agents, preservative, stabilizer, flavouring etc. or with a topical carrier. The compounds can also be formulated in compositions such as sterile solutions or suspensions for parenteral administration. Approximately 0.1 to 500 mg of a fungicide can be mixed with a physiologically tolerable carrier, excipients, binding agents, preservative, stabilizer etc. in a unit dose form, as is demanded by accepted pharmaceutical practice. The amount of the active substance in these compositions or preparations is preferably one in which a suitable dose in the range indicated is obtained.

Exemplary compositions for oral administration comprise suspensions which can contain, for example, microcrystalline cellulose for conferring mass, alginic acid or sodium alginate as a suspending agent, methylcellulose as a viscosity enhancer and sweetening agents or flavourings, such as those which are known in industry, and tablets with immediate release, which can contain, for example, microcrystalline cellulose, dicalcium phosphate, starch, magnesium stearate and/or lactose and/or other excipients, binding agents, extenders, disintegrants, diluents and lubricants, such as those which are known in industry. Moulded tablets, pressed tablets or freeze-dried tablets are exemplary forms which can be used. Exemplary compositions comprise those which formulate the fungicidal active substances with rapidly soluble solvents such as mannitol, lactose, sucrose and/or cyclodextrins. In formulations of this type, excipients of high molecular weight such as celluloses (Avicel) or polyethylene glycols (PEG) can also be present. Formulations of this type can also contain an excipient in order to assist the mucous membrane adhesion, such as hydroxypropylcellulose (HPC), hydroxypropylmethylcellulose (HPMC), sodium carboxymethylcellulose (SCMC), maleic anhydride copolymer (e.g. Gantrez) and means for the control of the release such as polyacrylic copolymers (e.g. Carbopol 934). Lubricants, glidants, flavourings, colouring agents and stabilizers can also be added for easier preparation and use.

The abovementioned fungicides can either be administered on their own or in combination with further other fungicides. Combinations of fungicides are especially useful which likewise have an action against fish mycoses, in order to safeguard the action accordingly and effectively to prevent the formation of resistance of the fungal pathogen to the active substance.

The checking of the efficacy of the treatment agents can be confirmed by laboratory tests or by experiments with experimental animals. The laboratory tests allow an exact characterization of the efficacy of the compounds according to their potency of action. For this, the active substances are added to an artificial culture medium and the fungal growth is determined after an incubation period. In animal experiments, for example, eggs from breeding fish are treated. For this, the treatment agents are added in a suitable concentration to the water tank in which the fish eggs are kept. This takes place, for example, by means of the flow of water which is added continuously to the incubation tank during the fish farming. After the supply of the treatment agent, the replacement of water is stopped for a certain time in order that the treatment agent can start to act. This treatment can be carried out once or continuously for a number of days or alternatively in a daily or number of days rhythm for minutes to a few hours. After this, the treatment agent is removed from the incubation tank by means of the replacement of water. The efficacy and the tolerability of the treatment is determined by means of the number of live and fungally uninfected eggs. The efficacy and the tolerability in hatched, developed fish or adult animals are tested in water tanks in which the fish are cultured. For this, the treatment agent is added to the fish tank. After the supply of the treatment agent, the replacement of water is stopped for a certain time in order that the treatment agent can begin to act. This treatment can be carried out once or continuously for a number of days or alternatively in a daily or number of days rhythm for minutes to a few hours. The efficacy and the tolerability of the treatment are determined by means of the number of live fish and the degree of fungal infection.

The invention is illustrated in more detail by the following example.

WORKING EXAMPLE

Example 1

Determination of the Efficacy of Substances Against Fish-Parasitic Fungi, for Example *Saprolegnia* spp.

An isolate of *Saprolegnia parasitica* (CBS 540.67, Centraalbureau voor Schimmelcultures, Baarn, Netherlands) is grown and replicated in the dark at 20° C. on PD agar (39 g/l final concentration). For the determination of the $ED_{50}$ value, PD agar plates are treated with a concentration series of 0-0.03-0.1-0.3-1-3-10-30 ppm of the fungicide to be tested. In each case, inoculation pieces containing *Saprolegnia parasitica* are placed in the centre of the petri dishes treated with the various concentrations of the fungicide.

The plates are incubated in the dark at 20° C. for three days and the growth of the fungus on the agar plate is then measured and the $ED_{50}$ values are calculated from the comparison with the untreated control.

In this test, for example, the fungicides fluoxastrobin, fenamidone, cyazofamid, famoxadone and pyribencarb show an $ED_{50}$ value of 5 ppm or less.

The invention claimed is:

1. A method of treating mycoses in fish, invertebrates, and all their stages of development, caused by fungi of the genera *Saprolegnia*, the method comprising contacting fish, invertebrates, and all their stages of development in need thereof, a composition comprising fluoxastrobin, with said fish, their habitat, or a combination thereof.

* * * * *